US00PP16735P2

(12) United States Plant Patent
Egger

(10) Patent No.: US PP16,735 P2
(45) Date of Patent: Jun. 27, 2006

(54) *HEUCHERA* PLANT NAMED 'TNHEU042'

(50) Latin Name: *Heuchera hybrida*
Varietal Denomination: TNHEU042

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 86 days.

(21) Appl. No.: 11/083,819

(22) Filed: Mar. 16, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—June Hwu
(74) *Attorney, Agent, or Firm*—Klarquist Sparkman, LLP

(57) ABSTRACT

A new and distinct *Heuchera* plant substantially as shown and described, characterized by lime green foliage, light pink flowers, and good vigor.

1 Drawing Sheet

Botanical denomination: *Heuchera hybrida.*
Variety designation: 'TNHEU042'.
Cross reference to: *Heuchera* 'Lime Rickey' (U.S. Plant patent application Ser. No. 10/871,417), a sibling.

The present invention relates to a new and distinct cultivar of *Heuchera hybrida* and given the cultivar name of 'TNHEU042'. *Heuchera* is in the family Saxifragaceae. *Heuchera* 'TNHEU042' originated from a cross between *Heuchera* 'Amber Waves' (U.S. Plant Pat. No. 13,348), as the seed parent, and *Heuchera* 'Huntsman', an unpatented plant, as the pollen parent. Given its ornamental foliage and flower form it is probable that *Heuchera micrantha, H. americana, H. brizoides,* and *H. sanguinea* are in its parentage.

This new *Heuchera* is distinguished by:

1. Lime green leaves summer through winter.
2. Chartreuse spring foliage.
3. Small light pink flowers.
4. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
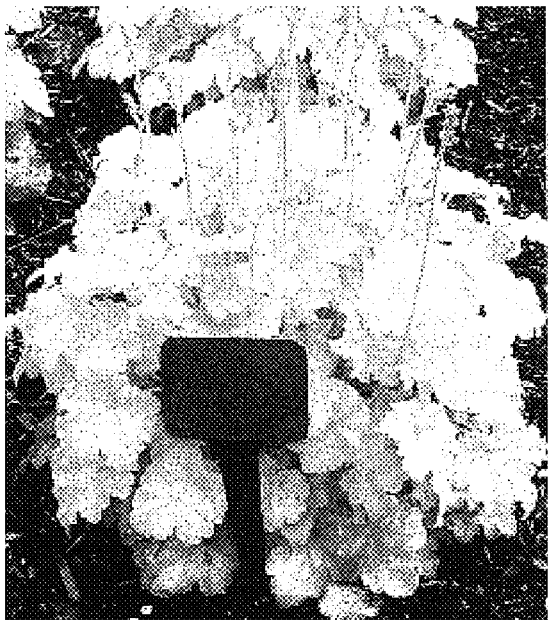
FIG. 1 shows a two year old *Heuchera* 'TNHEU042' in bloom, growing in the ground in the shade house in late spring in Canby, Oreg.
Figure 2:
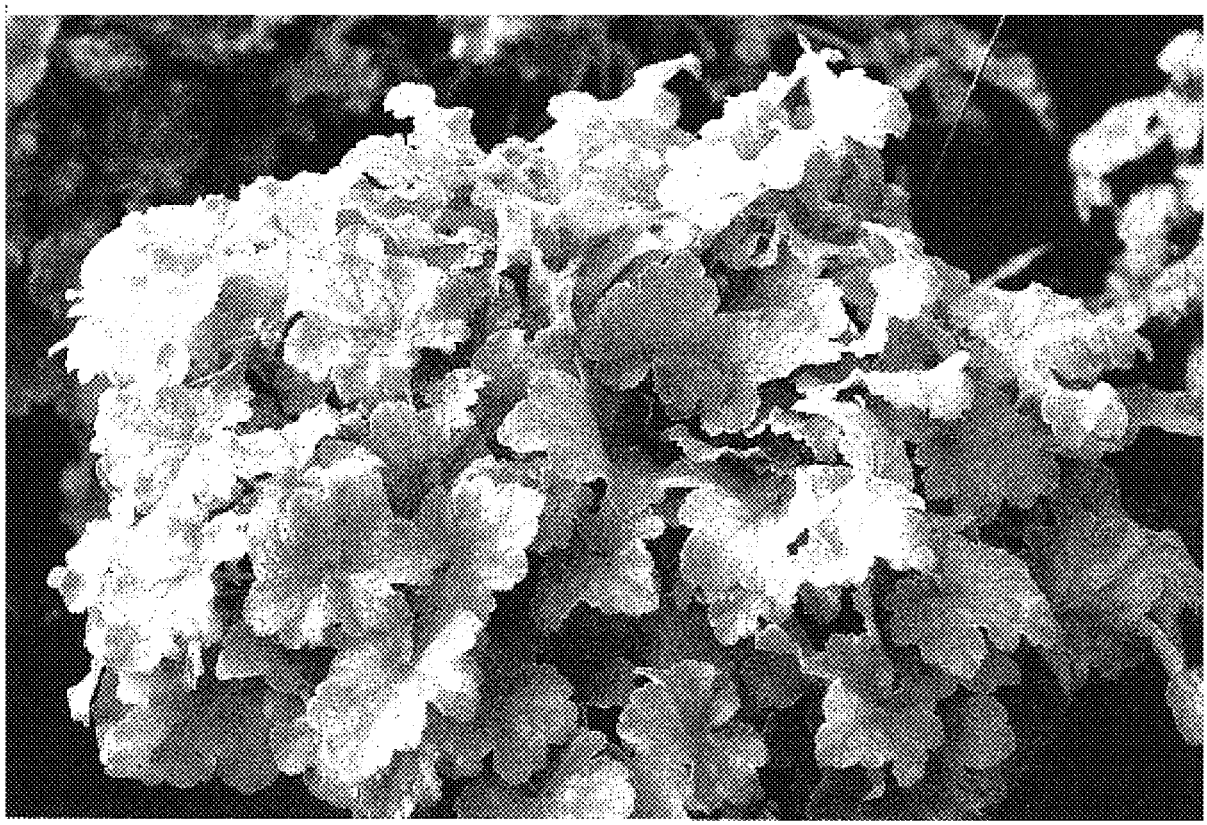
FIG. 2 shows *Heuchera* 'TNHEU042' in a one gallon container in the shade house in the fall in Canby, Oreg.

The following is a detailed description of the new *Heuchera* cultivar based on observations of a two-year-old specimen grown in the ground in an open air shade house with 50% shade cover and added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Botanical denomination: *Heuchera hybrida.*
Variety designation: 'TNHEU042'.
Parentage: *Heuchera* 'Amber Waves' U.S. Plant Pat. No. 13,348 (seed parent)×*Heuchera* 'Huntsman' (pollen parent).

Plant:
- *Form.*—Basal rosette, herbaceous perennial.
- *Hardiness.*—USDA Zone 4 to 9.
- *Size.*—20 cm tall from top of the foliage to the ground and 35 cm wide.
- *Habit.*—Mounding.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Ovate.
- *Lobing/division.*—3 main shallow lobes, with 2 to 3 shallow secondary lobes.
- *Venation.*—Palmate.
- *Margins.*—Crenate and incised.
- *Apex.*—Mucronulate.
- *Base.*—Cordate, lobes overlapping at the base.
- *Blade size.*—5 to 7 cm long and 5 to 7.5 cm wide.
- *Surface texture.*—Sparsely glandular both sides.
- *Texture.*—Thin, leathery.
- *Petiole size.*—11 to 16 cm long and 1.5 mm wide.
- *Petiole surface texture.*—Glandular hairs of various sizes.
- *Petiole color.*—Yellow Green 145B.
- *Leaf color.*—Spring newest growth, abaxial — Yellow 9A. Spring adaxial — Yellow Orange 14D. Summer, fall abaxial — Lime, Yellow 7D to between Yellow Green 145A and 151A. Winter abaxial — Lime, Yellow Green 144A, with red veins, Greyed Red 183A, and tan margins, Greyed Yellow 161A. Summer through winter adaxial — Yellow Green 151A to 145A.

Inflorescence:

*Size.*—6 to 9 cm wide and 17 to 28 cm long.

*Type.*—Thyrse.

*Number of flowers per thyrse.*—83 to 110 per thyrse.

*Number of thyrse.*—41 in spring bloom.

*Peduncle.*—40 to 63 cm tall, 3 mm wide at base, Yellow Green 151A, glandular hairs, with 3 to 4 petiolate cauline leaves (ovate, blades 2 to 5 cm long and 1 to 4 cm wide with a lobed and incised margin).

*Pedicel.*—Variable in size, with glandular hairs, Greyed Orange 163A to 174A.

*Bloom period.*—Late May to June in Canby, Oreg.

Flower bud:

*Size.*—2.5 mm wide and 5 mm long.

*Description.*—Glandular puberulent, ovoid.

*Color.*—Red Purple 62A at the tip and Greyed Yellow 160B at the base.

Flower:

*Type.*—Perfect, zygomorphic.

*Shape.*—Campanulate.

*Size.*—3 mm long and 3 mm wide.

*Petal description.*—5 in number, inconspicuous, 3.5 mm long, spatulate with a clawed base, reflexes slightly, tip acute, margin entire, White 155D on both sides.

*Calyx description.*—5 lobes, divided ⅓ way to the base, with glandular hairs, tip acute, margin entire, 4 mm long and 3 mm wide, Greyed Red 182C on both sides.

*Stamen description.*—5 in number, filaments White 155B, anther color is Orange 28B, pollen color is Orange 25C.

*Pistil description.*—White 155B overall, 2.5 mm long.

*Fragrance.*—None.

*Lastingness.*—Each thyrse blooms for about 2 weeks on the plant.

Fruit:

*Type.*—Two-beaked ovoid capsule.

*Size.*—3 mm deep by 2 mm wide.

*Fertility.*—Good.

*Color.*—Brown 200D.

Seed:

*Shape.*—Linear.

*Size.*—2 mm long.

*Color.*—Black, RHS 202A.

Disease and pest tolerance: Excellent disease resistance to powdery mildew, the common problem of *Heuchera*. All *Heuchera* are susceptible to root weevils.

COMPARISON TO SIMILAR *HEUCHERA*

Compared to its sibling, *Heuchera* 'Lime Rickey' (U.S. Plant patent application Ser. No. 10/871,417), this new variety has light pink flowers, rather than white, and leaves that are not ruffled, rather than ruffled.

Compared to the seed parent, *Heuchera* 'Amber Waves', the new variety has leaves that are lime green and unruffled rather than amber colored and ruffled. The new variety is also more vigorous and has light pink rather than creamy white flowers.

Compared to the pollen parent, *Heuchera* 'Huntsman', the new variety has leaves that are lime green overall rather than green with reddish centers and a light veil. Both have pinkish colored flowers.

I claim:

1. A new and distinct *Heuchera* plant as herein illustrated and described.

* * * * *